(12) United States Patent
Thoorens et al.

(10) Patent No.: US 7,998,505 B2
(45) Date of Patent: Aug. 16, 2011

(54) DRY GRANULATION BINDERS, PRODUCTS, AND USE THEREOF

(75) Inventors: Gregory Thoorens, Brussels (BE); Bruno Leclercq, Brussels (BE); Brian Carlin, Lawrenceville, NJ (US); Peter J. Riley, Yardley, PA (US); Miguel Angel Garcia, Newark, DE (US)

(73) Assignee: FMC Corporation, Philadelphia, PA (US)

( * ) Notice: Subject to any disclaimer, the term of this patent is extended or adjusted under 35 U.S.C. 154(b) by 251 days.

(21) Appl. No.: 11/925,375

(22) Filed: Oct. 26, 2007

(65) Prior Publication Data

US 2008/0213360 A1    Sep. 4, 2008

Related U.S. Application Data

(60) Provisional application No. 60/855,106, filed on Oct. 27, 2006, provisional application No. 60/855,066, filed on Oct. 27, 2006, provisional application No. 60/928,166, filed on May 8, 2007.

(51) Int. Cl.
A61K 9/20     (2006.01)
A61K 9/50     (2006.01)
A01N 25/00    (2006.01)

(52) U.S. Cl. .................. 424/465; 424/499; 514/781
(58) Field of Classification Search .................. 424/465, 424/499; 514/781
See application file for complete search history.

(56) References Cited

U.S. PATENT DOCUMENTS

| | | |
|---|---|---|
| 2,978,446 A | 4/1961 | Battista et al. |
| 3,145,146 A | 8/1964 | Lieberman et al. |
| 3,146,168 A | 8/1964 | Battista |
| 3,539,365 A | 11/1970 | Durand et al. |
| 3,573,058 A | 3/1971 | Tiemstra |
| 3,639,169 A | 2/1972 | Broeg et al. |
| 4,110,476 A | 8/1978 | Rhodes |
| 4,263,334 A | 4/1981 | McGinley |
| 4,264,637 A | 4/1981 | Braverman |
| 4,426,518 A | 1/1984 | Omiya |
| 4,693,750 A | 9/1987 | Bauer et al. |
| 4,744,987 A | 5/1988 | Mehra et al. |
| 4,980,193 A | 12/1990 | Tuason, Jr. et al. |

(Continued)

FOREIGN PATENT DOCUMENTS

EP    1226818 A1    7/2002

(Continued)

OTHER PUBLICATIONS

S. A. Mitchell, et al., A compaction process to enhance dissolution of poorly water-soluble drugs using hydroxypropyl methylcellulose, *International Journal Pharmaceutics*, 250, 3-11, 2003.

(Continued)

*Primary Examiner* — Robert A Wax
*Assistant Examiner* — Aradhana Sasan

(57) ABSTRACT

A method for the preparation of microcrystalline cellulose containing tablets by roller compaction followed by tabletting is disclosed. A tablet formulation is converted to a dry granulate by roller compaction, and the dry granulate is lubricated and compacted to a tablet. The tablet formulation comprises at least one active, an microcrystalline cellulose containing material, and, optionally other pharmaceutically acceptable excipients. The microcrystalline cellulose containing material has a maximum primary compaction tensile strength of at least 9 MPa or at least 9.5 MPa and a secondary compaction tensile strength of at least 5 MPa, at least 5.5 MPa, or at least 6 MPa. A method for evaluating binders is also disclosed.

7 Claims, 3 Drawing Sheets

U.S. PATENT DOCUMENTS

| | | |
|---|---|---|
| 5,082,684 A | 1/1992 | Fung |
| 5,192,569 A | 3/1993 | McGinley et al. |
| 5,272,137 A | 12/1993 | Blase et al. |
| 5,286,510 A | 2/1994 | Bauer et al. |
| 5,366,742 A | 11/1994 | Tuason, Jr. et al. |
| 5,409,907 A | 4/1995 | Blase et al. |
| 5,415,804 A | 5/1995 | Minami et al. |
| 5,505,982 A | 4/1996 | Krawczyk et al. |
| 5,573,777 A | 11/1996 | Serpelloni et al. |
| 5,605,712 A | 2/1997 | Bertrand et al. |
| 5,607,716 A | 3/1997 | Doherty et al. |
| 5,609,898 A | 3/1997 | Kaji et al. |
| 5,709,896 A | 1/1998 | Hartigan et al. |
| 5,725,886 A | 3/1998 | Erkoboni et al. |
| 5,747,067 A | 5/1998 | Auguello et al. |
| 5,769,934 A | 6/1998 | Ha et al. |
| 5,789,004 A | 8/1998 | Hogan et al. |
| 5,866,166 A | 2/1999 | Staniforth et al. |
| 6,010,734 A | 1/2000 | Whelan et al. |
| 6,025,007 A | 2/2000 | Krawczyk |
| 6,037,380 A | 3/2000 | Venables et al. |
| 6,079,630 A | 6/2000 | Schroeder |
| 6,106,865 A | 8/2000 | Staniforth et al. |
| 6,117,474 A | 9/2000 | Kamada et al. |
| 6,235,947 B1 | 5/2001 | Yoshinari et al. |
| 6,264,981 B1 | 7/2001 | Zhang et al. |
| 6,270,830 B1 | 8/2001 | Kamada et al. |
| 6,368,649 B1 | 4/2002 | van Bommel |
| 6,391,368 B1 | 5/2002 | Tuason et al. |
| 6,432,448 B1 | 8/2002 | Augello et al. |
| 6,440,474 B1 | 8/2002 | Buliga et al. |
| 6,475,539 B1 | 11/2002 | DeWille et al. |
| 6,500,462 B1 | 12/2002 | Augello et al. |
| 6,503,918 B2 | 1/2003 | Yoshinari et al. |
| 6,548,093 B1 | 4/2003 | Collinge et al. |
| 6,689,405 B1 | 2/2004 | Tuason et al. |
| 6,709,713 B2 | 3/2004 | Augello et al. |
| 6,723,342 B1 | 4/2004 | Augello et al. |
| 6,726,949 B2 | 4/2004 | Adolphi et al. |
| 6,752,939 B2 | 6/2004 | Gereg |
| 6,753,017 B2 | 6/2004 | Berkulin et al. |
| 6,936,277 B2 | 8/2005 | Staniforth et al. |
| 6,936,628 B2 | 8/2005 | Lee |
| 7,462,232 B2 | 12/2008 | Tuason et al. |
| 7,625,622 B2 | 12/2009 | Teckoe et al. |
| 7,785,089 B2 | 8/2010 | Teckoe et al. |
| 2003/0017204 A1 | 1/2003 | Augello et al. |
| 2003/0129238 A1 | 7/2003 | Augello et al. |
| 2004/0071821 A1 | 4/2004 | Ashourian et al. |
| 2004/0121006 A1 | 6/2004 | Narita et al. |
| 2004/0137043 A1 | 7/2004 | Augello et al. |
| 2004/0185161 A1 | 9/2004 | Ashourian et al. |
| 2005/0147710 A1 | 7/2005 | Teckoe et al. |
| 2005/0220824 A1 | 10/2005 | Kessel et al. |
| 2005/0233046 A1 | 10/2005 | Krawczyk et al. |
| 2005/0233053 A1 | 10/2005 | Shen et al. |
| 2005/0258827 A1 | 11/2005 | Patland et al. |
| 2005/0266116 A1 | 12/2005 | Teckoe et al. |
| 2006/0127451 A1 | 6/2006 | Augello et al. |
| 2007/0128333 A1 | 6/2007 | Tuason et al. |
| 2008/0131505 A1* | 6/2008 | Li et al. ............... 424/464 |
| 2008/0131543 A1 | 6/2008 | Teckoe et al. |
| 2009/0110799 A1 | 4/2009 | Funami et al. |
| 2009/0130287 A1 | 5/2009 | Tuason et al. |

FOREIGN PATENT DOCUMENTS

| | | |
|---|---|---|
| EP | 1-681-048 A1 | 7/2006 |
| GB | 1010477 | 11/1965 |
| GB | 1 567 049 | 5/1980 |
| GB | 2395413 | 5/2004 |
| JP | 08-151481 A2 | 6/1996 |
| JP | 9266779 | 10/1997 |
| JP | 10-056960 | 3/1998 |
| JP | 10-237220 | 9/1998 |
| JP | 11-046723 A2 | 2/1999 |
| JP | 11-299435 | 11/1999 |
| JP | 2000-184853 | 7/2000 |
| JP | 2001-190220 A | 7/2001 |
| JP | 2002/345401 A1 | 3/2002 |
| JP | 2002-125587 A | 5/2002 |
| JP | 2005-245217 | 9/2005 |
| WO | WO 81/02521 | 9/1981 |
| WO | 94/24888 A1 | 11/1994 |
| WO | WO 98/56826 | 12/1998 |
| WO | 00/04862 A2 | 2/2000 |
| WO | WO 01/19348 A1 | 3/2001 |
| WO | WO 0132150 | 5/2001 |
| WO | WO 0132152 | 5/2001 |
| WO | 02/49451 A2 | 6/2002 |
| WO | WO 03/003843 A1 | 1/2003 |
| WO | 03/096976 A2 | 11/2003 |
| WO | WO 03/090558 A1 | 11/2003 |
| WO | WO 2005/030177 A2 | 4/2005 |
| WO | 2005/096832 A2 | 10/2005 |
| WO | WO 2006-131963 A1 | 12/2006 |

OTHER PUBLICATIONS

P. Kleinebudde, Roll compaction/dry granulation: pharmaceutical applications, *European Journal of Pharmaceutics and Biopharmaceutics*, 58, 317-326, 2004.

Tracey L. Deyampert Rogers, Oral Preliminary Examination, Sep. 1, 1995.

Tracey L. Deyampert Rogers, Content Considerations for Low Dosage Drug Formulations Processed by Roller Compaction, Ph.D. Thesis, Purdue University, Aug. 1997.

Angela Marie Falzone, Roller compaction of pharmaceutical excipients and excipient-drug blends, Ph.D. Thesis, Purdue University, Dec. 1990.

G.W. Skinner, The evaluation of fine-particle hydroxypropylcellulose as a roller compaction binder in pharmaceutical applications, *Drug Development & Indus. Pharm*, 25(10), 1121-1128 (1999).

Introduction to Roll Compaction and the Fitzpatrick Chilsonator, The Fitzpatrick Company Europe N.V., Mar. 1997.

P. Sheskey, et al., Roll compaction Granulation of a Controlled-Release Matrix Tablet Formulation Containing HPMC, *Pharmaceutical Technology*, Oct. 1999.

Y. Zhang, et al., Physical Properties and Compact Analysis of Commonly Used Direct Compression Binders, *AAPS Pharm. Sci. Tech.*, 4 (4), Article 62, Dec. 15, 2003.

PJ Weller, et al., (Cellulose, Microcrystalline—XP-002-481910) "Handbook of Pharmaceutical Excipients, fourth edition", 2003, Pharmaceutical Press, London, p. 108-111.

The International Search Report and Written Opinion of the International Searching Authority, International Application No. PCT/US2007/022684, International Filing Date Oct. 26, 2007.

Hsiu -O H. et al. "Characteristics of Codried Products of Microcrystalline Cellulose with Saccharides and Low-substituted Hydroxypropylcellulose". Powder Technology, 127 (2002), pp. 45-53.

Gohel M. C. "A Review of Co-processed Directly Compressible Excipients". Journal of Pharm. Pharmaceut. Sci. 8(1), pp. 76-93, 2005.

Schroder R. et al. "Influence of Magnesium Stearate on the Compaction Behavior and Tablet Characteristics of Co-Spray Dried Compounds vs Physical Blends". Poster presented at American Association of Pharmaceutical Science (Denver) Oct. 2001.

Jacob S. et al. "Novel Co-processed Excipients of Mannitol and Microcrystalline Cellulose for Preparing Fast Dissolving Tablets of Glipizide". Indian Journal of Pharmaceutical Sciences, vol. 69(5) Sep.-Oct. 2007, pp. 633-639.

* cited by examiner

DRY GRANULATION BINDERS, PRODUCTS, AND USE THEREOF

CROSS-REFERENCE TO RELATED APPLICATIONS

This application claims priority on U.S. Provisional Application Ser. No. 60/855,106, filed Oct. 27, 2006, on U.S. Provisional Application Ser. No. 60/928,166, filed May 8, 2007, and on U.S. Provisional Application Ser. No. 60/855,066, filed Oct. 27, 2006, the disclosures of which are all incorporated herein by reference.

FIELD OF THE INVENTION

The present invention relates to dry granulation binders with high recompactability for the manufacture of solid dosage forms by multiple compaction processes. In particular, this invention relates to microcrystalline cellulose based binders where the binder ensures good granulate quality, and sufficient recompactability of the granules to obtain tablets of desired tensile strength.

BACKGROUND OF THE INVENTION

Discrete dosages of pharmaceutical compositions suitable for oral administration are conveniently administered as solid dosage forms, typically tablets. In addition to the therapeutic ingredient or ingredients (commonly referred to as "actives," "active pharmaceutical ingredients," or "API"), the tablet comprises pharmaceutically acceptable materials, known as excipients, that are not actives and do not provide a therapeutic effect, but are added to the tablet formulation to confer specific properties not related to the activity of the active.

There are three general methods of preparation of tablets: (1) direct compression; (2) dry granulation; and (3) wet granulation. In direct compression, the powdered material(s) to be included in the tablet (including the active and the excipients) are blended together and compressed directly without intermediate processing, such as granulation. Although direct compression is the most effective and favorable manufacturing process for the production of solid dosage forms, such as tablets, many tablet formulations cannot be processed using direct compression due.

Granulation procedures may be used where poor flow or low bulk density of the direct compression mix precludes tabletting by direct compression. Granulation also improves content uniformity of the active, and reduces dust generation. Dry granulation includes mixing the ingredients, roller compacting or slugging the mix, dry screening or milling to a coarse dry granulate, lubricating, and compressing the lubricated granules. The wet granulation procedure includes mixing some or all of the ingredients and thereafter adding solutions of a binding agent to the mixed powders. The resulting wet mass is screened, dried, lubricated, and compressed into tablets.

In dry granulation, the tablet ingredients are not exposed to moisture, solvents and heat. Thus, it can be used to process moisture, solvent and/or heat sensitive actives. Dry granulation can be carried out by slugging or by roller compaction. Slugging is a double compression process. The material to be tabletted is compressed to a large compressed mass, or "slug," which is converted to tablets by a second compression process. Because slugging is a slow and uneconomic process, roller compaction has become the method of choice for dry granulation. Roller compaction has all the benefits of a granulation process, such as improved material flow behavior and content uniformity. In addition, roller compaction is high-volume and more economical to operate than wet granulation.

During the roller compaction process, at least a portion of the tablet formulation (the "granulate formulation") is compacted and densified by two counter-rotating high-pressure rollers, and the resulting material milled to uniform size. The resulting granulate may be subsequently tabletted with or without additional excipients to form tablets. The tablet is formed by pressure acting on the tablet formulation in a die on a tablet press. A tablet press includes a lower punch which fits into a die from the bottom and an upper punch having a corresponding shape and dimension, which enters the die cavity from the top after the tablet formulation fills the die cavity. The tablet is formed by pressure applied to the tablet formulation in the die by the lower and upper punches.

Because of its inherent compactability characteristics, microcrystalline cellulose (MCC) finds widespread use as an excipient in pharmaceutical formulations. Good binding and disintegration properties are also obtained when MCC is used in tablet formulations.

Tablet formation by roller compaction followed by tabletting includes two compaction steps. However, after the first compaction step, the MCC granulate may have insufficient compactability for the second compaction, i.e., tabletting, step. Therefore a need exists for microcrystalline containing binders that can be used to prepare solid dosage forms by processes involving multiple compaction steps such as roller compaction and tabletting, or slugging. The binder must have sufficient compactability for the second compaction step.

SUMMARY OF THE INVENTION

The invention is a microcrystalline cellulose containing binder with improved recompactability, such that it can be used in the manufacture of solid dosage forms by multiple compaction processes. In one aspect, the invention is a composition that comprises at least 60 wt % of a microcrystalline cellulose containing material and has a primary tensile strength of at least 9.5 MPa after a primary compaction at 250 MPa and has a secondary tensile strength of at least 5.5 MPa following secondary compaction at 250 MPa after a primary compaction at 250 MPa. In another aspect, the invention is a binder composition comprising at least 60 wt % of a microcrystalline cellulose containing material, the binder composition having primary tensile strength of at least 9.0 MPa after a primary compaction at 250 MPa and a secondary tensile strength of at least 5.0 MPa following secondary compaction at 250 MPa after a primary compaction pressure at 250 MPa, in which the MCC containing material is microcrystalline cellulose co-processed with a material selected from the group consisting of sugar alcohols and carboxymethyl cellulose.

In another aspect, the invention is a binder composition comprising at least 60 wt % of a microcrystalline cellulose containing material, the binder composition having primary tensile strength of at least 9.5 MPa after a primary compaction at 250 MPa and a maximum secondary tensile strength of at least 6.0 MPa following secondary compaction after a primary compaction pressure at 250 MPa. In another aspect, the MCC containing material is microcrystalline cellulose co-processed with a material selected from the group consisting of sugar alcohols and carboxymethyl cellulose.

In another aspect, the invention is a binder composition comprising at least 60 wt % of a microcrystalline cellulose containing material, the binder composition having a maximum secondary tensile strength of at least 6.5 MPa following secondary compaction after a primary compaction pressure at 250 MPa, in which the MCC containing material is microcrystalline cellulose co-processed with a material selected from the group consisting of sugar alcohols and carboxymethyl cellulose.

Granulate formulations, granules, solid dosage forms; and tablets that comprise the microcrystalline cellulose containing binders of the invention are also aspects of the invention. In other aspects, the invention includes methods for preparing granulate formulations, granules, solid dosage forms, and tablets that comprise the microcrystalline cellulose containing binder of the invention. In another aspect, the invention is a method of testing, evaluating, and selecting binders, especially binders that comprise at least about 40 wt %, or at least about 60% or at least about 65 wt %, of a microcrystalline cellulose containing material, to determine which binders have a high primary compaction and a high secondary compaction and, thus, can be used to prepare solid dosage forms by direct compaction.

DETAILED DESCRIPTION OF THE INVENTION

Unless the context indicates otherwise, in the specification and claims, the terms active, excipient, sugar alcohol, and similar terms also include mixtures of such materials. Unless otherwise specified, all percentages are percentages by weight and all temperatures are in degrees Centigrade (degrees Celsius). Compression/compressibility refers to the ability of a powder to densify under pressure, while the terms compaction/compactability refer to the ability to yield granules or tablets with specific properties as a result of the compression. Microcrystalline cellulose containing material and MCC containing material refer to materials that are at least about 40 wt % microcrystalline cellulose. Such materials may comprise more than 40 wt % microcrystalline cellulose, for example, at least about 50 wt % microcrystalline cellulose, at least about 60 wt % microcrystalline cellulose, at least about 65 wt % microcrystalline cellulose, at least about 70 wt % microcrystalline cellulose, and at least about 75 wt % microcrystalline cellulose.

Dry Granulation

The solid dosage forms comprise the MCC containing material of the invention, one or more actives, and, optionally, one or more one or more pharmaceutically acceptable excipients and/or lubricants. Solid dosage form manufacture using dry granulation requires two compaction steps. The first occurs during roller compaction or slugging, when the granulation binder-containing formulation is compacted to form granules. The second occurs during formation of the solid dosage form, or tabletting, when the tablet formulation, which contains the granules, is compacted into a tablet.

The art teaches that microcrystalline cellulose shows reduced compactability after repeated compaction events. After the first compaction, porosity of the microcrystalline cellulose is reduced and is associated with reduced compactability of the compacted microcrystalline cellulose relative to the microcrystalline cellulose before the first, or primary, compaction. Thought not being bound by any theory or explanation, it is thought that a number of hydrogen bonds are formed during the primary compaction, reducing the number of potential hydrogen bonding sites for the second or subsequent compactions.

Figure 1:
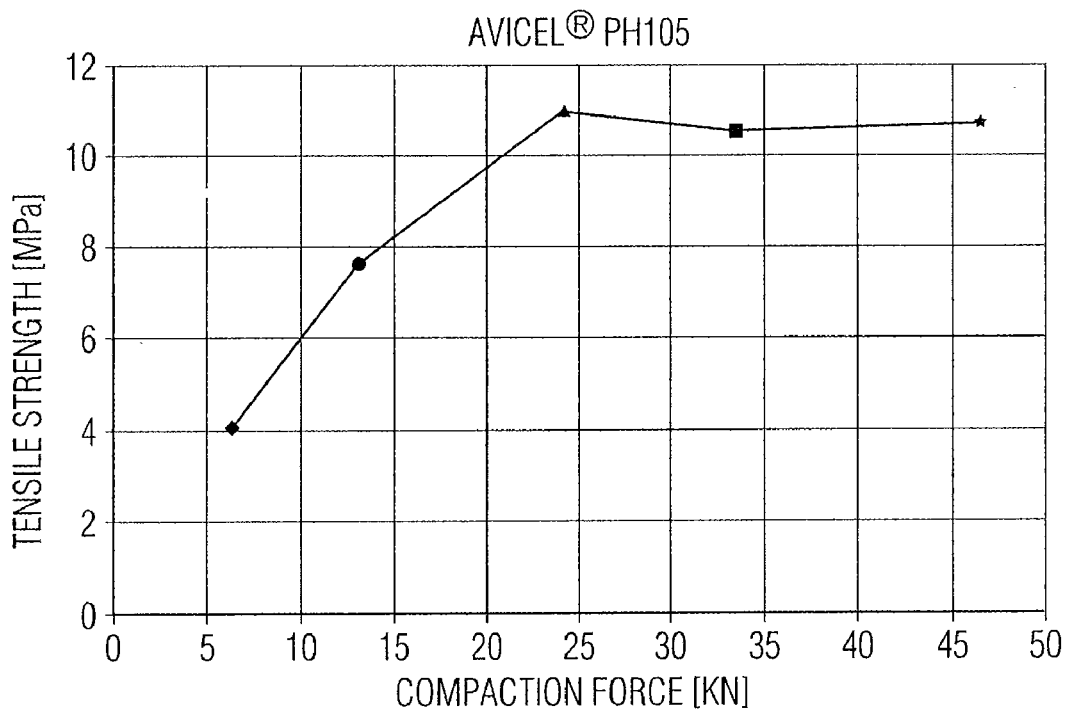
FIG. 1 shows the tensile strength of the tablet against primary compaction pressure for microcrystalline cellulose (AVICEL® PH-105 grade) at five different pressures levels.

However, it has been found that when microcrystalline cellulose containing materials undergo primary compaction, the tensile strength of the resulting material increases as the compaction pressure increases, but reaches a limiting value, or plateau, at higher compaction pressures. This can be seen in FIG. 1, which shows the tensile strength of ribbons formed from compaction of AVICEL® PH-105 microcrystalline cellulose at five different primary compaction forces (6.3 kN, 13 kN, 24 kN, 33 kN, and 46 kN). These primary compaction forces correspond to primary compaction pressures of about 50 MPa, about 100 MPa, about 185 MPa, about 250 MPa, and about 350 MPa, respectively. A plateau is reached when the primary compaction pressure is about 200 MPa. Upon application of higher pressure, the tensile strength does not increase significantly, and may even decrease slightly.

Figure 2:
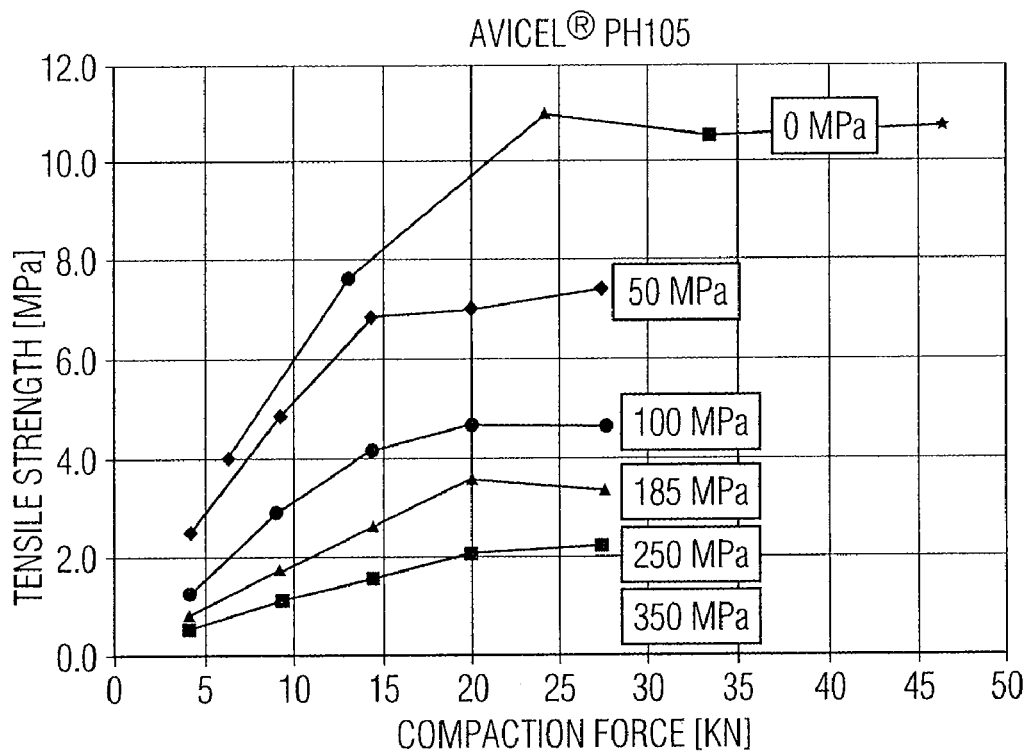
FIG. 2 is a plot of the tensile strength of the tablet against secondary compaction pressure for AVICEL® PH-105 microcrystalline cellulose processed at different primary compaction pressures.

FIG. 2 show the tensile strength vs. secondary compaction force for the tablets from dry granulates prepared at the range of primary compaction pressures. The secondary compaction forces of 4 kN, 9 kN, 14 kN, 19 kN, and 27 kN correspond to secondary compaction pressures of about 50 MPa, about 115 MPa, about 180 MPa, about 240 MPa, and about 350 MPa, respectively. The primary compaction pressure for each curve is shown in the box to the right of each line. The "0 MPa" curve shows material that was not recompacted (i.e. direct compression, primary compaction only), which is equivalent to a secondary compaction in which the primary compaction force was 0 MPa The remaining curves were obtained by recompaction of materials that were previously compacted at the indicated primary compaction pressure levels. These primary compaction pressures correspond to primary compaction forces shown in FIG. 1. A progressive fall off of secondary compactability ("recompactability") can be seen, which is dependent upon the pressure used for the primary compaction. Increasing the primary compaction pressure causes "overcompaction", which causes the secondary compaction tensile strength to decrease.

For use in tablet formation by roller compaction followed by tabletting, the MCC containing material should have secondary compaction tensile strength of at least 5.5 MPa, preferably 6.0 MPa, having undergone a primary compaction of 250 MPa and a secondary compaction of 250 MPa, i.e., the secondary compaction tensile strength is measured on MCC containing material that has undergone primary compaction at a pressure approaching or on the plateau in primary tensile strength.

In one aspect, the composition may have a primary tensile strength of at least 9.5 MPa after a primary compaction at 250 MPa and a secondary tensile strength of at least 5.5 MPa following a primary compaction at 250 MPa and secondary compaction at 250 MPa. In another aspect, the composition may have a primary tensile strength of at least 9.5 MPa after a primary compaction at 250 MPa and a maximum secondary tensile strength of at least 6.0 MP after a primary compaction pressure at 250 MPa and secondary compaction. Maximum tensile strength following secondary compaction is typically attained by a secondary compaction of about 350 MPa.

When the microcrystalline cellulose has been co-processed with a sugar alcohol or with a carboxymethyl cellulose, the composition may have a primary tensile strength of at least 9.0 MPa after a primary compaction at 250 MPa and a secondary tensile strength of at least 5.0 MPa after a primary compaction pressure at 250 MPa and a secondary compaction at 250 MPa. In another aspect, when the microcrystalline cellulose has been co-processed with a sugar alcohol or with carboxymethyl cellulose, the composition has a maximum secondary tensile strength of at least 6.5 MPa after a primary compaction at 250 MPa and secondary compaction.

Several materials have been shown to satisfy this criterion. Co-processed mixtures of sugar alcohols and MCC, such as are described below, satisfy this criterion. Co-processed MCC:mannitol (about 85:15), for example, has a primary compaction tensile strength of 10.0 MPa and a secondary compaction tensile strength maximum of 6.2 MPa. Co-processed MCC:mannitol (about 75:25) has a primary compaction tensile strength of 9.5 MPa and a secondary compaction tensile strength maximum of 5.5 MPa. Co-processed MCC: mannitol (about 95:5) has a primary compaction tensile strength of 10.0 MPa and a secondary compaction tensile strength maximum of 5.5 MPa. Co-processed MCC/carboxymethyl cellulose (CMC) has a primary compaction tensile strength of 10.0 MPa and a secondary compaction tensile strength maximum of 5.5 MPa.

Although a secondary compaction tensile strength of at least 5.5 MPa is somewhat greater than the tensile strength generally required for tablets, typically about 2 MPa, these values refer to secondary tensile strengths measured on compact tablets containing only the unformulated MCC containing material rather than secondary tensile strengths for MCC containing materials that have been formulated in tablets. It is anticipated that the tensile strengths of tablets formulated with these MCC containing materials and other ingredients will be somewhat lower.

Roller Compaction

Roller compaction (also known in the art as "roll compaction") is a dry compaction/granulation process of tablet formation, which is used when a tablet formulation does not have the flow characteristics or high enough bulk density necessary for tablet formation. A roller compactor uses pressure to compact and densify the tablet formulation and to bind powders into granules. Actives that have been processed by roller compaction include, for example, acetylsalicylic acid (aspirin), acetaminophen, amoxicillin, ibuprofen, penicillin, ranitidine, and streptomycin.

Figure 3:
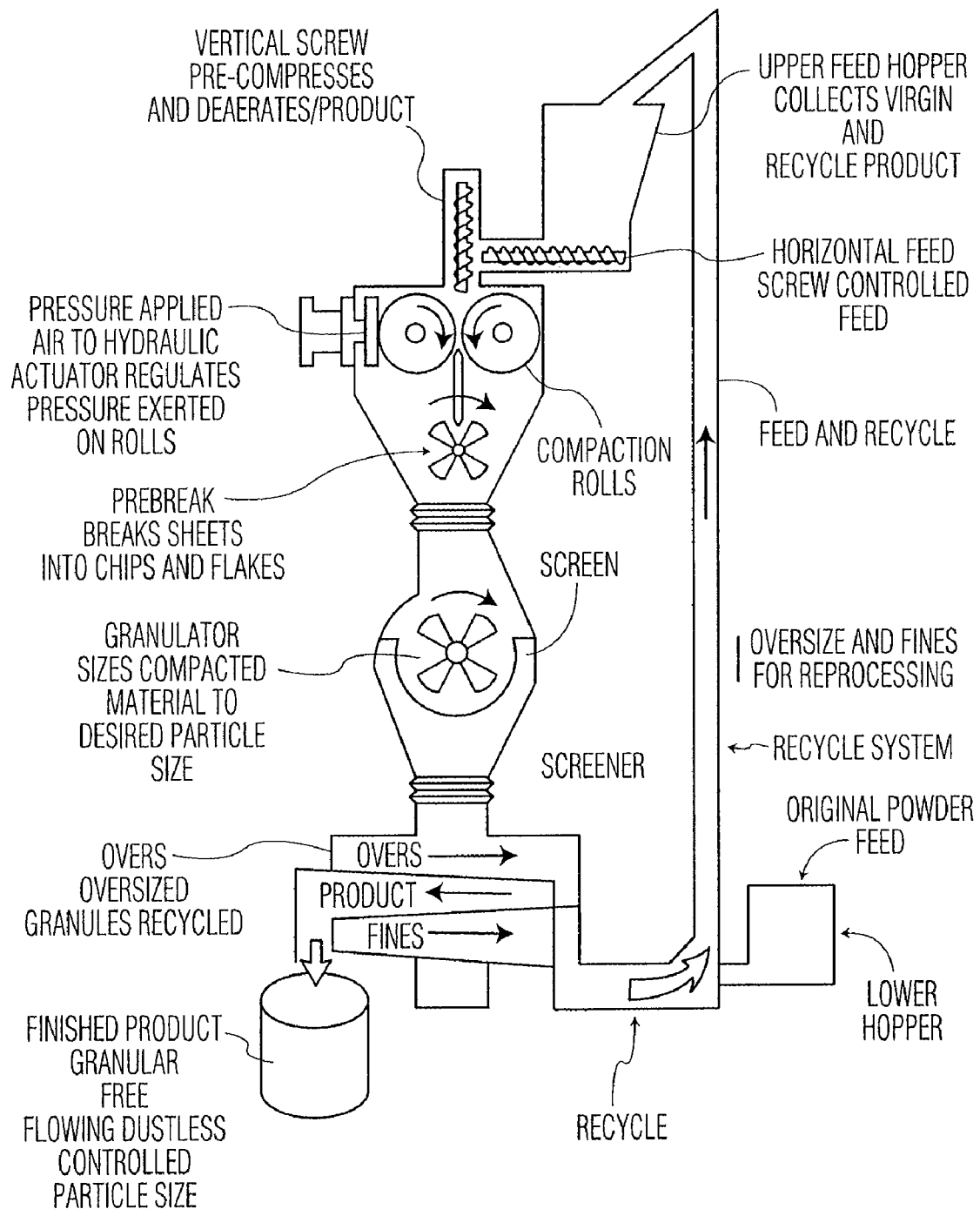
FIG. 3 is a schematic representation of a roller compaction system that provides a continuous process for the granulation of tablet formulations.

Granulation is a process of size enlargement in which small particles are gathered together into larger aggregates in which the original particles can still be identified. Uniformly mixed powders (granulate formulations) are compressed between counter rotating rollers to form a ribbon of compacted material that is then milled into granules. A schematic representation of a roller compactor is shown in FIG. 3. A roller compactor comprises a roller assembly, press frame, hydraulic pressure system, and a feed system. The feed system is located immediately before the rollers and determines the rate of flow of the granulate formulation to the rollers. The feed system may comprise one or more feed screws that force the granulate formulation between the compacting rollers. The granulate formulation is compacted as it passes through the two compacting rollers. The volume of the granulate formulation decreases as it passes through the region of maximum pressure, where it is formed into a solid compacted material known as a sheet or ribbon. Compaction pressure is provided by the hydraulic pressure system, which can be adjusted to produce the desired compaction pressure. The hydraulic pressure system acts on one of the rollers. As shown in FIG. 3, the roller compaction process may be a continuous process of compacting, milling, screening, and recycling the too large granules ("Overs") and too small granules ("Fines") back to the process.

Various configurations for the rollers are well known in the art and are described, for example, in A. M. Falzone, Ph.D. Thesis, Purdue University, 1990 (U.M.I., Ann Arbor, Mich., Order Number 9313940). Roller compaction equipment is commercially available from the Fitzpatrick Company, Elmhurst Ill. USA as CHILSONATOR® roll compactors. This equipment is described in "Introduction to Roll Compaction and the Fitzpatrick CHILSONATOR," published by The Fitzpatrick Company Europe.

Tabletting

Tabletting is well known to those skilled in the art of tablet formation. The tablet is formed by pressure being applied to the tablet formulation on a tablet press. A tablet press includes a lower punch which fits into a die from the bottom and an upper punch having a corresponding shape and dimension, which enters the die cavity from the top after the tablet formulation fills the die cavity. The tablet is formed by pressure applied to the tablet formulation in the die by the lower and upper punches. The ability of the tablet formulation to flow freely into the die is important in order to ensure that there is a uniform filling of the die with continuous flow of tablet formulation from hopper to die. Typically, a lubricant, such as magnesium stearate, is added to facilitate ejection of the tablet from the die following compaction, and to avoid sticking to the punch faces. Tabletting is well described in pharmaceutics textbooks such as AGENNARO, Remington: The Science and Practice of Pharmacy, 20th Ed., Lippincott Williams & Wilkins, Baltimore, Md., 2000.

Microcrystalline Cellulose

Microcrystalline cellulose (MCC) is purified, partially depolymerized cellulose, which may be obtained by hydrolysis of various cellulose sources, such as wood, wood pulps such as bleached sulfate and sulfate pulps, cotton, flax, hemp, bast or leaf fibers, regenerated forms of cellulose, soy hulls, corn hulls, or nut hulls. It is a white, odorless, tasteless, relatively free flowing powder that is insoluble in water, organic solvents, dilute alkalis and dilute acids.

Hydrolysis may be accomplished by any of several well-known methods. Generally, the source of cellulose, preferably a source of alpha-cellulose, in the form of a pulp from fibrous plants, is treated with a mineral acid, preferably hydrochloric acid. The acid selectively attacks the less ordered regions of the cellulose polymer chain, thereby leaving the more crystalline regions, which constitute microcrystalline cellulose. The MCC is then separated from the reaction mixture and washed to remove by-products. The resulting wet mass, generally containing 40-60 wt % moisture, is referred to by several names, including hydrolyzed cellulose, microcrystalline cellulose, microcrystalline cellulose wetcake, or simply wetcake. Preparation of microcrystalline cellulose is disclosed in Battista, U.S. Pats. No. 2,978,446 and 3,146,168.

Microcrystalline cellulose is commercially available under the trade name EMCOCEL® from Edward Mendell Co., Inc. and as AVICEL® from FMC Corp. Several grades of microcrystalline cellulose that vary in particle size, density and moisture content are available, for example, AVICEL® PH-101, PH-102, PH-103, PH-105, PH-112, PH-113, PH-200, PH-301, and PH-302.

Co-Processed Composition

The co-processed composition comprises two components, MCC and a sugar alcohol. The two components are present at a weight ratio of about 99:1 to 1:99 microcrystalline cellulose:sugar alcohol. When MCC is co-processed with a sugar alcohol, such as mannitol, the weight ratio of the two components, MCC:sugar alcohol, is preferably about 70:30 to 95:5, more preferably 75:25 to 90:10.

Sugar alcohol refers to polyhydroxy alcohols that include acyclic or alicyclic polyols. Acyclic sugar alcohols have the general formula $C_nH_{n+2}(OH)_n$. Typical sugar alcohols include, for example, mannitol, sorbitol, xylitol, lactitol, isomalt, maltitol, erythritol, and threitol. Preferred sugar alcohols are those containing four to six carbon atoms (i.e, n is 4 to 6), especially five or six carbon atoms (n is 5 or 6).

A particularly preferred sugar alcohol is mannitol [$(C_6H_8(OH)_6)$] [(2R,3R,4R,5R)-hexane-1,2,3,4,5,6-hexol] [CAS # 69-65-8]. Mannitol is non-hydroscopic, produces solutions with relatively low viscosity, and has a relatively high melting point (about 167-170° C.). These properties allow aqueous microcrystalline cellulose/mannitol slurries to be readily spray dried to produce co-processed microcrystalline cellulose/mannitol.

The co-processed composition is a particulate composition that has an average mean particle size of about 20 microns to about 1000 microns. The mean particle size is typically about 50 microns to about 200 microns, more typically about 70 microns to about 120 microns, and even more typically 80 microns to 110 microns, for example, about 90 microns. The loose bulk density (LBD) of the co-processed product is typically less than or equal to 0.60 g/cm$^3$. The loose bulk density of the co-processed product, with a component ratio of 70:30 to 95:5 microcrystalline cellulose:mannitol, for example, is typically about 0.35-0.50 g/cm$^3$. The pH is about 3.0 to about 8.5, preferably about neutral. When carboxymethyl cellulose is used, the composition may comprise at least 80 wt % MCC, at least 85 wt % MCC, at least 90 wt %, or at least 95 wt % MCC.

The preparation and properties of co-processed microcrystalline cellulose:sugar alcohol compositions is described in co-filed United States Patent Application FMC Docket Number 60560-USA, "Co-Processed Microcrystalline Cellulose and Sugar Alcohol as an Excipient for Tablet Formulations," incorporated herein by reference.

Co-Processing

The process for preparing the co-processed composition involves forming a well-dispersed aqueous slurry of MCC and a sugar alcohol, for example mannitol. The relative amounts of the two components are adjusted in the slurry to yield the specific weight ratio desired in the final dried co-processed product. Then the aqueous slurry is dried by removing water from it to yield the co-processed product. Preferably, the slurry is dried using spray-drying techniques, which are well known in the art. Other drying techniques, however, such as flash drying, ring drying, tray drying, vacuum drying, radio frequency drying, and microwave drying, can also be used.

The MCC is preferably wetcake from a conventional MCC manufacturing process. Wetcake is MCC that has not yet been dried to yield conventional MCC as a free-flowing powder. Alternatively, dried MCC may be re-hydrated to produce an aqueous slurry of MCC. The particle size of the MCC used in the aqueous slurry is ordinarily that which is encountered in conventional MCC manufacture.

The aqueous slurry of these two components may be prepared in any of several ways. The sugar alcohol may be introduced into the microcrystalline cellulose slurry as solid or pre-dissolved in water. Typically the solids concentration is about 5-25 wt % microcrystalline cellulose, preferably about 10-20 wt % microcrystalline cellulose. The exact amount of sugar alcohol to be added depends on the MCC content of the slurry and the ratio of the two components desired in the co-processed product. Water may also be added if a more dilute slurry is required. The total solids content of the aqueous slurry is preferably at least 10 wt %, based on the total slurry weight, and is more preferably at least 20 wt % solids. The higher solids content levels are desirable since the amount of water that must be removed during the drying step is accordingly reduced. The upper limit on solids content in the aqueous slurry is typically determined by the operating constraints of the drying apparatus used. With the preferred spray drying procedure, solids contents of 20-30 wt % are representative for aqueous slurries that can be readily processed. Ambient or elevated slurry temperatures, of from about 10° C.-80° C. may be used, and higher slurry temperatures may be desirable with certain types of drying equipment.

The drying of the well-dispersed aqueous slurry is preferably accomplished by spray drying. Conventional spray drying equipment may be used. Operating procedures familiar to those skilled in the spray drying art are applicable to the spray drying step of this process. Drier outlet temperature is ordinarily used to control the residual moisture level obtained in the co-processed composition. Depending upon the amount and type of drying, the concentration of the MCC and sugar alcohol in the slurry the co-processed product will have different particle sizes, densities, pH and moisture content. For this reason the drying step in the co-processing procedure is especially critical, and for this reason spray drying is the preferred method for drying.

Spray drying the slurry produces a co-processed composition having a loose bulk density of less than or equal to 0.60 g/cm$^3$, suitably 0.20 g/cm$^3$ to 0.60 g/cm$^3$. This produces a composition having a preferred compactability in the presence of lubricant and a preferred recompactability compared to either a dry blend of the materials or the corresponding wet granulate. The loose bulk density may be less than 0.55 g/cm$^3$, less than 0.50 g/cm$^3$, less than 0.45 g/cm$^3$, less than 0.40 g/cm$^3$, less than 0.35 g/cm$^3$, less than 0.30 g/cm$^3$, and less than 0.25 g/cm$^3$. The co-processed product recovered from the drying operation is a free-flowing particulate solid. Particle size of the product is a function of the spray drier settings, which can be controlled by those skilled in the art by adjusting feed rates and atomizer disc speeds during spray drying.

Solid Dosage Forms

The solid dosage form comprises the MCC containing material of the invention, one or more actives, and, optionally, one or more one or more pharmaceutically acceptable excipients. Typical tablet formulations are prepared by combining the active or actives with at least one excipient according to conventional pharmaceutical compounding techniques. To prepare a solid dosage form, or tablet, by direct compaction, the tablet formulation must have the necessary physical characteristics. Among other things, the tablet formulation must be free flowing, must be lubricated, and, importantly, must possess sufficient compactability to ensure that the solid dosage form remains intact after compaction, and is robust enough for subsequent operations, such as handling, coating, and packaging.

The tablet is formed by pressure being applied to the tablet formulation on a tablet press. A tablet press includes a lower punch that fits into a die from the bottom and an upper punch having a corresponding shape and dimension that enters the die cavity from the top after the tablet formulation fills the die cavity. The tablet is formed by pressure applied on the lower and upper punches. The ability of the tablet formulation to flow freely into the die is important in order to ensure that there is a uniform filling of the die and a continuous movement of the material from the source of the tablet formulation, e.g. a feeder hopper. The lubricity of the tablet formulation is crucial in the preparation of the solid dosage forms because the compressed material must be readily released from the punch faces. The tablet must also eject cleanly from the die following compression.

Because actives do not always have these properties, methods of tablet formulation have been developed in order to impart these desirable characteristics to the tablet formulation. Typically, the tablet formulation comprises one or more additives, or excipients, that impart the desired free flowing, lubrication, and binding properties to the tablet formulation.

The excipients for dry granulate formulations should have good recompactability and dilution potential to allow compaction of the granules into a tablet. The excipients should not accelerate chemical and/or physical degradation of the active and should not interfere with its biological availability. The excipients should be physiologically inert and should not unintentionally interfere with the tablet disintegration or dissolution of the active. They should show low lubricant sensitivity and ensure acceptable active content uniformity. Typical excipients are selected from the group consisting of a disintegrants, glidants, fillers, diluents, colorants, flavorants, stabilizers, and lubricants. The choice of the excipients and the composition of the tablet formulation depend on the active, the amount of active in the formulation, the type of tablet, the desired characteristics for both the tablet formulation and the resulting tablet, and the manufacturing process used. These include prompt release, for which the drug dissolves in a very short time, immediate release and modified release, which include most of the orally administered tablets that are swallowed.

Pharmaceutically acceptable excipients are well known to those skilled in the art and are disclosed for example, in Staniforth, U.S. Pat. No. 6,936,277, and Lee, U.S. Pat. No. 6,936,628. MCC is added to improve the compactability of the tablets. Excipients such as diluents, binders, glidants, and lubricants are added as processing aids to make the tabletting operation more effective. Still other types of excipients enhance or retard the rate of disintegration of the tablet, improve the taste of the tablet, (for example, sweetening agents), or impart a color or flavor to the tablets.

Lubricants are typically added to prevent the formulation from sticking to the punches during tablet manufacture. Commonly used lubricants include magnesium stearate and calcium stearate. Lubricants typically comprise about 0.5 wt % to about 3.0 wt % of the formulation. Antiadherents prevent sticking of the tablet formulation to the punch face and die wall. They are used in combination with magnesium stearate when sticking is a problem. Commonly used antiadherents are cornstarch and talc. Diluents, fillers, or bulking agents are frequently added in order to increase the bulk weight of the material to be tabletted in order to make the tablet a practical size. This is often necessary where the dose of the active is relatively small. Typical fillers include lactose, dicalcium phosphate, calcium carbonate, powdered cellulose, dextrates, mannitol, starch, pre-gelatinized starch, and mixtures thereof. Sugar alcohols, such as, sorbitol, mannitol and xylitol are also used as fillers, especially in chewable tablet formulations. The most significant differences between sorbitol and mannitol are hygroscopicity and solubility. Sorbitol is hygroscopic above 65% relative humidity and mannitol is nonhygroscopic. The aqueous solubility of sorbitol is higher than mannitol.

Binders are added to impart cohesive qualities to the powdered material(s). Commonly used binders include starch, microcrystalline cellulose, and sugars such as sucrose, glucose, dextrose, and lactose. Stabilizers reduce the rate at which the active decomposes. Typical stabilizers are antioxidants such as ascorbic acid. Disintegrants are often added to ensure that the tablet has an acceptable dissolution rate in an environment of use (such as the gastrointestinal tract). The disintegrant breaks up the tablets and the granules into particles of active and excipients. Although MCC and partially pregelatinized starch are frequently used in formulations to perform both the functions of compaction and disintegration it is often necessary to add super-disintegrants such as croscarmellose sodium, sodium starch glycolate, or crospovidone.

Glidants are used in tablet formulations to improve flow. They are more frequently used in dry blend, rather than wet granulated formulations. Because of the shape and size of the particles, glidants improve flow in low concentrations. They are mixed in final tablet formulation in dry form. Most commonly used glidants are alkali metal stearates, colloidal silicon dioxide (CAB-O-SIL®, SYLOID®, AEROSIL®), and talc.

Desirable characteristics may be imparted to the tablet by colorants (i.e., dyes and pigments), natural or artificial sweeteners, and flavorants. Wetting agents, also called surface active agents or surfactants, may also be present. The tablet may also be coated.

The size of round tablets is typically about 50 mg to 500 mg and for capsule-shaped tablets about 200 mg to 1200 mg. However, other formulations prepared in accordance with the invention may be suitably shaped for other uses or locations, such as other body cavities, e.g., periodontal pockets, surgical wounds, and vaginally. For certain uses, such as chewable tablets, antacid tablets, vaginal tablets, and implants, the tablet may be larger.

The compositions are also suitable use in the NRobe® process to prepare solid dose forms. Solid dose forms for the NRobe® process are prepared by lightly compacting a tablet formulation or granulate formulation to form a powder compact and enrobing the powder compact with a film. Methods and apparatus for forming the enrobed solid dose forms are disclosed in WO 03/096963, WO 2005/030115, WO 2005/030116, WO 2005/030379, and WO 2006/032828, the disclosures of which are all incorporated herein by reference.

INDUSTRIAL APPLICABILITY

The MCC containing materials of the invention are used as binders in solid dosage forms, such as tablets, that comprise one or more actives, and optionally, one or more other excipients. They are particularly useful as binders for formulations prepared by direct compression. Although primarily used in pharmaceutical and veterinary applications, they may be used in other areas, such as agriculture, food, cosmetics, and other industrial applications.

The advantageous properties of this invention can be observed by reference to the following examples, which illustrate but do not limit the invention.

EXAMPLES

| Glossary | |
|---|---|
| AVICEL ® PH-101 | 50 Micron microcrystalline cellulose (FMC, Philadelphia, PA USA) |
| AVICEL ® PH-105 | 20 Micron microcrystalline cellulose (FMC, Philadelphia, PA USA) |
| AVICEL ® PH-200 | 180 Micron microcrystalline cellulose (FMC, Philadelphia, PA USA) |
| AVICEL ® PH-302 | High density 90 micron microcrystalline cellulose (FMC, Philadelphia, PA USA) |
| AVICEL ® RC-591 | Co-processed colloidal grade MCC:NaCMC (sodium carboxymethyl cellulose) (89:11), (FMC, Philadelphia PA) |
| CELLACTOSE ® | 75:25 α-Lactose monohydrate/25% MCC (Meggle Pharm, Waserburg, Germany) |
| TCP | Tricalcium phosphate |
| ETHOCEL ® A4C | Methylcellulose (Dow Chemical, Midland MI USA) |
| EMCOMPRESS® | Calcium hydrogen phosphate dihydrate (JRS Pharam LP, Patterson, NY USA) |
| GRANULAC ® 200 | Lactose monohydrate, 96% of particles less than 100 microns (Meggle Pharm, Waserburg, Germany) |
| KOLLIDON ® 90F | Polyvinylpyrrolidone (BASF, Ludwigshaften am Rhein, Germany) |
| Lactose monohydrate NF | (Foremost Farms, Sparta, WI USA) |
| Magnesium stearate | (Mallinckrodt, St. Louis, MO USA) |
| MicroceLac 100 | Co-processed MCC:Lactose (25:75) (Meggle Pharma, Waserburg, Germany) |
| Parteck 150 | Directly compressible sorbitol (Merck KGaA, Darmstadt, Germany) |
| PEARLITOL ® 100 SD | Granular mannitol (100 microns) (Roquette Freres, Lestrem, France) |
| PEARLITOL ® 300 DC | Granular mannitol (250 microns) (Roquette Freres, Lestrem, France) |
| PEARLITOL ® 400 DC | Granular mannitol (360 microns) (Roquette Freres, Lestrem, France) |
| PEARLITOL ® 500 DC | Granular mannitol (520 microns) (Roquette Freres, Lestrem, France) |
| PROSOLV ® 90 | Silicified microcrystalline cellulose (JRS Pharma, Patterson NY USA) |
| StarLac | Spray-dried compound consisting of 85% α-lactose monohydrate and 15% maize starch (Meggle Pharm, Waserburg, Germany) |
| Sorbolac 400 | α-Lactose monohydrate (Meggle Pharma, Waserburg, Germany) |
| TABLETTOSE ® 100 | α-Lactose-monohydrate (Meggle Pharma, Waserburg, Germany) |
| VITACEL ® L600 | Powdered cellulose ORS Pharma, Patterson NY USA) |
| VITACEL ® VE-650 | Co-processed MCC:Calcium Carbonate (65:35) (FMC, Philadelphia, PA USA) |

General Procedures

The following procedure was used to measure the primary tensile strength and the secondary tensile strength. Each bulk test material was compacted at five different compaction pressure levels to produce a compact. Compaction was carried out on a special pneumohydraulic tablet machine "Flexi-iTab" as a roller compaction simulator. The compacts are round, flat tablets (13 mm, 750 mg). The crush strength of each compact was measured, and the tensile strength calculated. The compacts were milled to granules with a narrow particle size distribution (<1 mm).

To determine recompactability, each of the five resulting granulates was compacted as five different compaction pressure levels to produce round, flat tablets (10 mm, 500 mg). The crush strength of each tablet was measured and the tensile strength calculated.

Example 1

This example shows that a co-processed MCC/sugar alcohol mixture has a higher secondary compaction tensile strength maximum than a physical mixture of the same ingredients in the same proportions.

Figure 4:
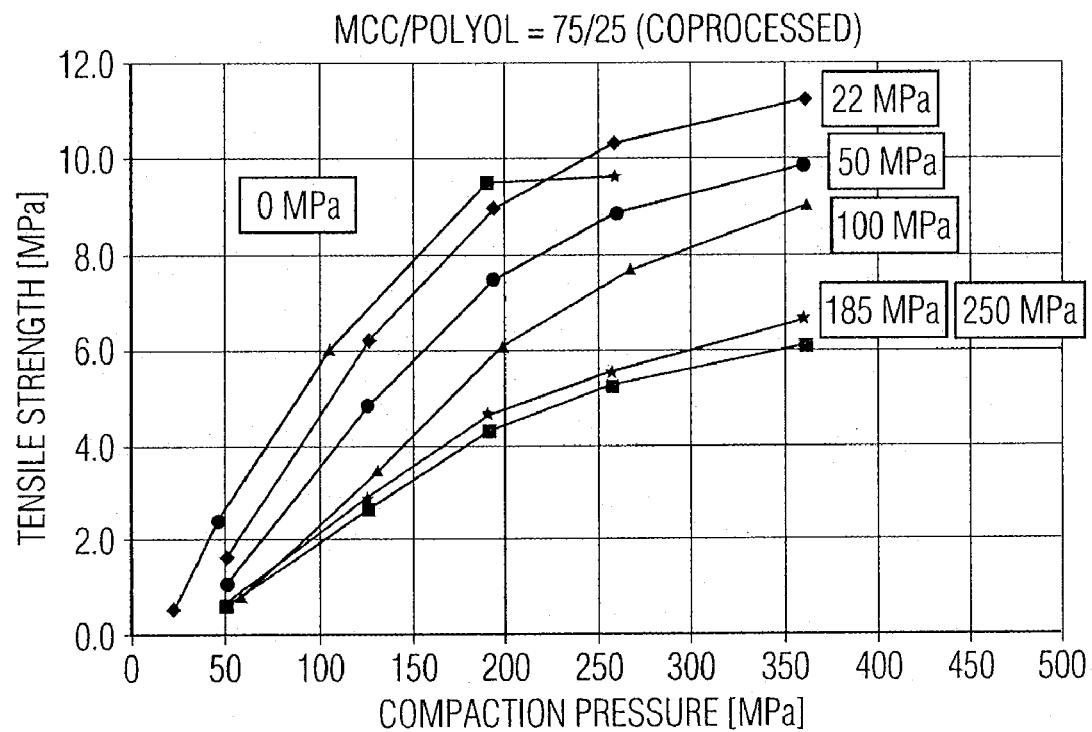
FIG. 4 is a plot of the tensile strength of the tablet against secondary compaction pressure for a co-processed 75:25 mixtures of MCC/mannitol processed at different primary compaction pressures.
Figure 5:
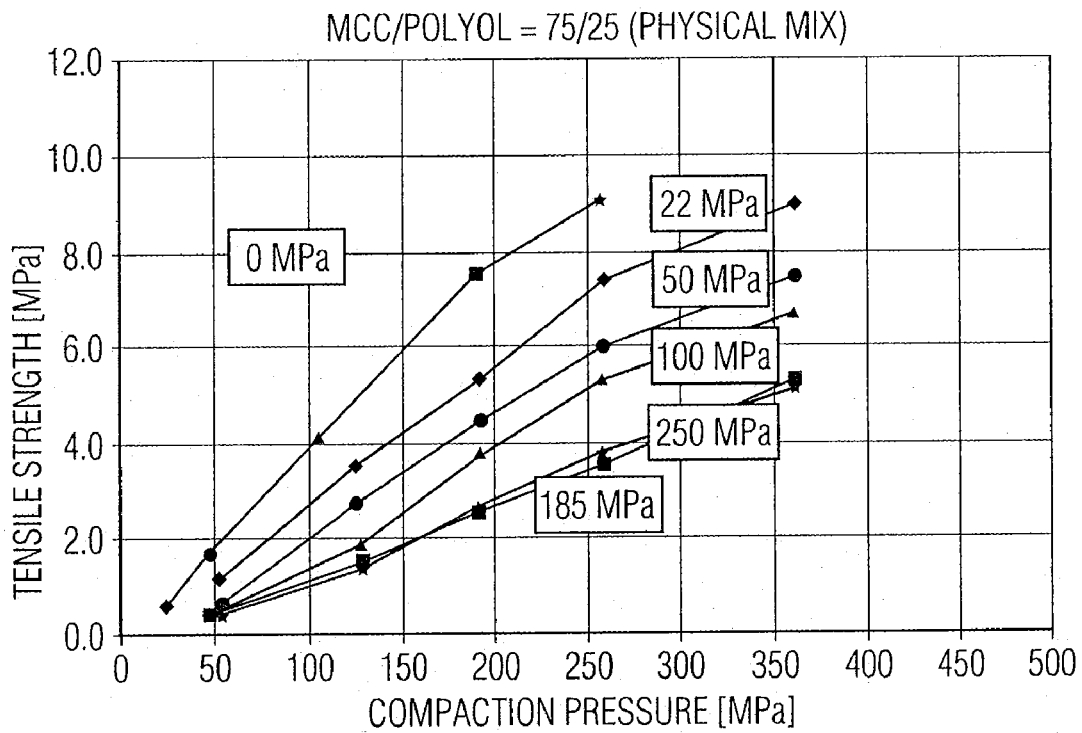
FIG. 5 is a plot of the tensile strength of the tablet against secondary compaction pressure for 75:25 dry blends (i.e., non-co-processed physical mixtures) of MCC/mannitol processed at different primary compaction pressures.

A co-processed 75:25 mixture of MCC/mannitol was prepared by adding mannitol to MCC wetcake and spray drying the slurry. The co-processed 75:25 mixture of MCC/mannitol and a 75:25 non-co-processed, physical mixture of MCC/mannitol were each evaluated as described in the general procedures. The results for the co-processed mixture are shown in FIG. 4. The results for the physical mixture are shown in FIG. 5.

The co-processed MCC:mannitol has a maximum primary compaction tensile strength of 9.5 MPa. The maximum secondary compaction tensile strength was 6.5 MPa. In contrast, the physical mixture of MCC and mannitol has a maximum primary compaction tensile strength of 9.0 MPa and a maximum secondary compaction tensile strength of 5.0 MPa.

Example 2

Co-processed MCC:CMC was prepared at 4% of AQUALON® 7HF grade of sodium carboxyl methylcellulose (e.g. 4 g of CMC per 100 g MCC) by the following procedure, which does not subject the MCC to high shear conditions. MCC wetcake was dispersed in deionized water to prepare a 15% slurry. The slurry was heated to 60° C., and the slurry pH was adjusted to 8 using ammonia. Sufficient calcium chloride was added to the slurry to achieve a concentration of 0.01 moles/liter and then stirred 5 min using a LIGHTNIN'® mixer. Powdered CMC was added to the mixture while stirring with sufficient agitation to disperse the CMC and then the batch was spray dried under processing conditions to give a particle size comparable to AVICEL® PH-101

Example 3

A variety of materials were evaluated using the General Procedures. The tensile strength on primary compaction (primary tensile strength) after a primary compaction of 250 MPa and the maximum tensile strength on secondary compaction (secondary tensile strength) for each material are given in Table 1 along with the values for the materials prepared and/or evaluated in Examples 1 and 2.

TABLE 1

| | Tensile Strength (MPa) | | |
|---|---|---|---|
| Material | Primary[a] | Secondary[b] | Secondary[c] |
| Co-processed MCC:Mannitol (85:15) | 10.0 | 6.2 | 6.5 |
| Co-processed MCC:Mannitol (75:25) | 9.5 | 5.5 | 6.5 |
| Co-processed MCC:CMC (96:4) | 10.0 | 5.5 | 6.0 |
| Co-processed MCC:Mannitol (95:5) | 10.0 | 5.5 | 6.0 |
| VITACEL ® VE-650 | 9.0 | 6.5 | 6.5 |
| Methocel A4C | 6.0 | 5.0 | 5.0 |
| MicroceLac 100 | 8.0 | 4.5 | 5.5 |
| AVICEL ® PH-101 + 25% Methocel A4C (mixture) | 7.5 | 4.5 | 5.0 |
| PROSOLV ® SMCC 90 | 10.0 | 4.5 | 4.5 |
| CELLACTOSE ® | 6.5 | 4.0 | 5.0 |
| AVICEL ® PH-200 | 9.5 | 4.0 | 4.5 |
| AVICEL ® PH-101 + 25% Parteck SI (mixture) | 10.0 | 4.0 | 4.5 |
| AVICEL ® PH-101 + 25% Kollidon 90F (mixture) | 10.0 | 4.0 | 4.0 |
| Physical mixture of MCC and Mannitol (75:25) | 9.5 | 3.5 | 5.0 |
| AVICEL ® PH-302 | 8.5 | 3.5 | 4.0 |
| MCC:Alginate (95:5) | 9.0 | 3.0 | 4.0 |
| AVICEL ® PH-101 | 10.0 | 3.0 | 3.0 |
| Sorbolac 400 | 3.5 | 2.5 | 3.5 |
| Starlac | 5.0 | 2.5 | 3.5 |
| AVICEL ® RC-591 | 3.5 | 2.5 | 3.0 |
| TABLETTOSE ® 100 | 3.0 | 2.2 | 3.0 |
| VITACEL ® L600 (powdered cellulose) | 7.5 | 2.2 | 2.5 |
| AVICEL ® PH-101 + 25% TCP (mixture) | 6.5 | 2.0 | 3.0 |
| GRANULAC ® 200 | 2.5 | 2.0 | 3.0 |
| EMCOMPRESS ® | 2.0 | 2.0 | 3.0 |
| AVICEL ® PH-105 | 10.5 | 2.0 | 2.0 |

[a]After a 250 MPa primary compaction.
[b]After a 250 MPa primary compaction and a 250 MPa secondary compaction.
[c]Maximum tensile strength, measured after a 250 MPa primary compaction and a secondary compaction at about 350 MPa.

Having described the invention, we now claim the following and their equivalents.

What is claimed is:

1. A composition, wherein:
the composition comprises at least 60 wt % of a microcrystalline cellulose containing material,
the microcrystalline cellulose containing material consists of microcrystalline cellulose co-processed with carboxymethyl cellulose;
the composition has a primary tensile strength of at least 9.0 MPa after a primary compaction at 250 MPa, and
the composition has a secondary tensile strength of at least 5.0 MPa after a primary compaction at 250 MPa and a secondary compaction at 250 MPa.

2. A granulate formulation comprising the composition of claim 1, at least one active, and at least one lubricant.

3. A method comprising the steps of:
applying pressure to a granulate formulation to form a compact, and milling the compact to form a granulate; wherein:
the granulate formulation comprises a binder composition, at least one active, at least one excipient, and at least one lubricant,
the binder composition comprises at least 60 wt % of a microcrystalline cellulose containing material,
the microcrystalline cellulose containing material consists of microcrystalline cellulose co-processed with carboxymethyl cellulose, the binder composition has a maximum primary tensile strength of at least 9.0 MPa after a primary compaction at 250 MPa and a secondary tensile strength of at least 5.0 MPa after a primary compaction at 250 MPa and a secondary compaction after a primary compaction at 250 MPa.

4. The method of claim 3 in which the step of applying pressure is carried out by roller compaction.

5. The method of claim 3 additionally comprising the step of compacting the granules to form a solid dosage form.

6. A solid dosage form prepared by:
applying pressure to a granulate formulation to form a compact,
milling the compact to form a granulate; and
compacting the granules to form a solid dosage form;
wherein:
the granulate formulation comprises a binder composition, at least one active, at least one excipient, and at least one lubricant,
the binder composition comprises at least 60 wt % of a microcrystalline cellulose containing material, and
the microcrystalline cellulose containing material consists of microcrystalline cellulose co-processed with carboxymethyl cellulose, the binder composition has a maximum primary tensile strength of at least 9.0 MPa after a primary compaction at 250 MPa and a secondary tensile strength of at least 5.0 MPa after a primary compaction at 250 MPa and a secondary compaction after a primary compaction at 250 MPa.

7. The solid dosage form of claim 6 in which the solid dosage form has a tensile strength of at least 2 MPa.

* * * * *